(12) United States Patent
Schneider et al.

(10) Patent No.: US 9,795,741 B2
(45) Date of Patent: Oct. 24, 2017

(54) ASSEMBLY FOR A DRUG DELIVERY DEVICE AND DRUG DELIVERY DEVICE

(75) Inventors: Christiane Schneider, Frankfurt am Main (DE); Tobias Stever, Frankfurt am Main (DE); Michael Harms, Frankfurt am Main (DE); Ulrik Jakobi, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 659 days.

(21) Appl. No.: 14/113,859

(22) PCT Filed: May 4, 2012

(86) PCT No.: PCT/EP2012/058178
§ 371 (c)(1),
(2), (4) Date: Oct. 25, 2013

(87) PCT Pub. No.: WO2012/152666
PCT Pub. Date: Nov. 15, 2012

(65) Prior Publication Data
US 2014/0052075 A1    Feb. 20, 2014

(30) Foreign Application Priority Data

May 6, 2011 (EP) .................................. 11165042

(51) Int. Cl.
*A61M 5/00* (2006.01)
*A61M 5/31* (2006.01)
(Continued)

(52) U.S. Cl.
CPC ................ *A61M 5/31* (2013.01); *A61M 5/24* (2013.01); *A61M 5/31525* (2013.01);
(Continued)

(58) Field of Classification Search
CPC ...... A61M 5/24; A61M 5/31; A61M 5/31525; A61M 5/31542; A61M 5/31551;
(Continued)

(56) References Cited

U.S. PATENT DOCUMENTS 533,575 A    2/1895  Wilkens
5,226,895 A    7/1993  Harris
(Continued)

FOREIGN PATENT DOCUMENTS

EP    0937471    8/1999
EP    0937476    8/1999
(Continued)

OTHER PUBLICATIONS

International Search Report for Int. App. No. PCT/EP2012/058178, dated Aug. 30, 2012.

*Primary Examiner* — Kevin C Sirmons
*Assistant Examiner* — Leah Swanson
(74) *Attorney, Agent, or Firm* — McDonnell Boehnen Hulbert & Berghoff LLP

(57) ABSTRACT

An assembly for a drug delivery device is provided comprising a housing, a cartridge holder releasably connectable to the housing, a resilient member, and an interaction member which is configured to mechanically cooperate with the resilient member and with the cartridge holder. The resilient member is configured to rotationally bias the interaction member. The assembly has a locked state where the cartridge holder is connected to the housing, the cartridge holder being obstructed from movement with respect to the housing, and an unlocked state where the connection between the cartridge holder and the housing is released, the cartridge holder being freely moveable with respect to the housing.

20 Claims, 7 Drawing Sheets

(51) Int. Cl.
*A61M 5/24* (2006.01)
*A61M 5/315* (2006.01)

(52) U.S. Cl.
CPC .... *A61M 5/31543* (2013.01); *A61M 5/31551* (2013.01); *A61M 5/31585* (2013.01); *A61M 5/31535* (2013.01); *A61M 5/31541* (2013.01); *A61M 5/31575* (2013.01); *A61M 2005/2407* (2013.01); *A61M 2005/2477* (2013.01); *A61M 2005/2488* (2013.01); *A61M 2205/581* (2013.01); *A61M 2205/582* (2013.01)

(58) Field of Classification Search
CPC ......... A61M 5/31585; A61M 5/31535; A61M 5/31575; A61M 2005/2407; A61M 2005/2477; A61M 2005/2488; A61M 5/31543; A61M 5/31541; A61M 2205/581; A61M 2205/582
USPC ....................................................... 604/207
See application file for complete search history.

(56) References Cited

U.S. PATENT DOCUMENTS

| | | | |
|---|---|---|---|
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2009/0247951 A1* | 10/2009 | Kohlbrenner ........... A61M 5/20 604/134 |
| 2009/0275916 A1 | 11/2009 | Harms et al. |
| 2009/0312717 A1* | 12/2009 | Christiansen ........... A61M 5/24 604/232 |

FOREIGN PATENT DOCUMENTS

| | | |
|---|---|---|
| EP | 1923083 | 5/2008 |
| WO | 99/38554 | 8/1999 |
| WO | 01/10484 | 2/2001 |
| WO | 2008/009646 | 1/2008 |
| WO | 2008/031235 | 3/2008 |
| WO | 2010/139640 | 12/2010 |

\* cited by examiner

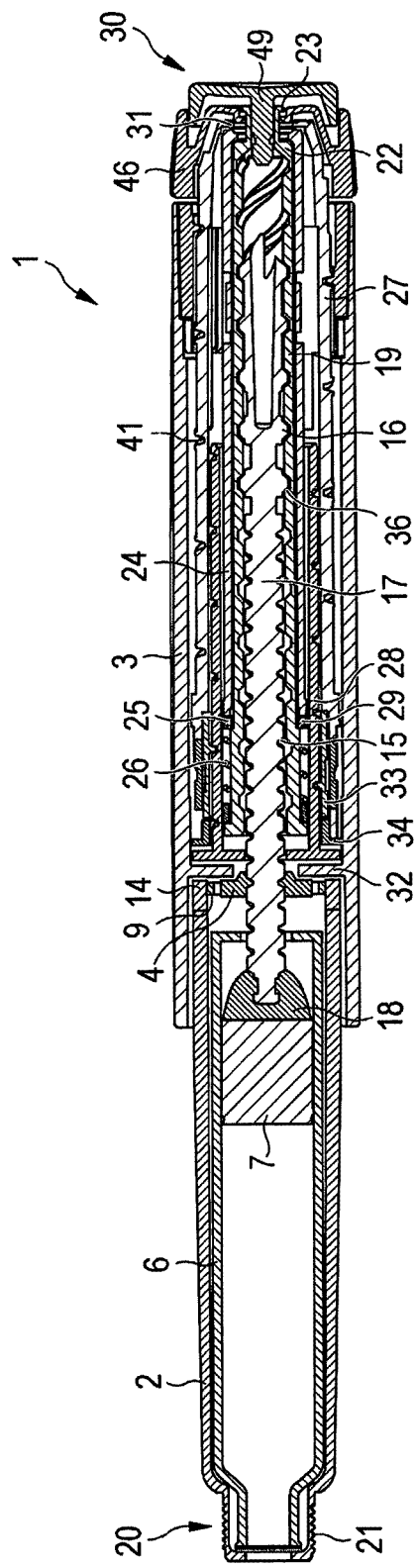

ASSEMBLY FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2012/058178 filed May 4, 2012, which claims priority to European Patent Application No. 11165042.0 filed May 6, 2011. The entire disclosure contents of these applications are herewith incorporated by reference into the present application.

FIELD OF DISCLOSURE

This disclosure relates to an assembly for a drug delivery device. Furthermore, the disclosure relates to a drug delivery device comprising such an assembly.

BACKGROUND

In a drug delivery device, often, a bung within a cartridge containing a plurality of doses of a drug is displaced by a piston rod. Thereby, a dose of the drug is expelled from the cartridge.

A drug delivery device is described in document EP 1 923 083 A1, for example.

SUMMARY

It is an object of the present disclosure to provide an assembly for an improved drug delivery device, for example a device with increased safety for the user. Furthermore, an improved drug delivery device is provided.

This object may be achieved by the subject matter of the independent claims. Advantageous embodiments and refinements are subject matter of the dependent claims.

One aspect relates to an assembly for a drug delivery device. The assembly may comprise a housing. Furthermore, the assembly may comprise a cartridge holder. The cartridge holder may be connectable, preferably releasable connectable, to the housing. Furthermore, the assembly may comprise a resilient member. Furthermore, the assembly may comprise an interaction member. The interaction member may be configured to mechanically cooperate with the resilient member. The interaction member may be configured to mechanically cooperate with the cartridge holder. The resilient member or an additional resilient member may be configured to rotationally bias the interaction member. The assembly may have a locked state and an unlocked state. In the locked state, the cartridge holder is preferably releasable connected to the housing. In the locked state, the cartridge holder may be obstructed from movement with respect to the housing. In the unlocked state, the connection between the cartridge holder and the housing may be released. In the unlocked state, the cartridge holder may be moveable with respect to the housing. For switching from the unlocked state into the locked state, the cartridge holder may be brought into mechanical cooperation with the interaction member. The cartridge holder may be rotated in a first direction with respect to the housing. Thereby, the interaction member may be rotated in the first direction such that the interaction member mechanically cooperates with the resilient member. Thereby, a rotational force exerted on the interaction member by means of the resilient member may be overcome for switching the assembly from the unlocked state into the locked state.

The assembly may have two defined states, which are the locked state and the unlocked state. The user can immediately realize when the assembly is in the unlocked state as, in the unlocked state, the cartridge holder is freely moveable with respect to the housing. In this way, an erroneous dose setting or delivery operation when the assembly is in the unlocked state, which may lead to underdosing, can be prevented. User safety is increased in this way.

The resilient member may comprise a spring force. The resilient member may be configured to exert a temporary rotational force on the interaction member. Especially during the switching procedure, e.g. when switching the assembly from the unlocked state into the locked state, a rotational force is exerted on the interaction member. The rotational force may be dependent on the angular path travelled by the interaction member when the assembly is switched from the locked state into the unlocked state. This rotational force must be overcome by the rotational force exerted onto the cartridge holder for completely performing the switching operation, i.e. for firmly securing the cartridge holder to the housing. In particular, the rotational force exerted onto the interaction member may provide a threshold value for the torque to perform the switching operation. Hence, the assembly may stay in the unlocked state unless a sufficiently high rotational force is exerted onto the cartridge holder for switching the assembly into the locked state. In this way, unintentional switching of the assembly from the unlocked state into the locked state can be prevented. This may further help to increase user safety of the assembly.

For switching the assembly from the unlocked state into the locked state, the interaction member may be rotationally locked to the cartridge holder. Thus, the interaction member can easily be brought into mechanical cooperation with the resilient member when the cartridge holder is rotated in the first direction. No further steps for achieving the mechanical cooperation between the interaction member and the resilient member are needed.

According to an embodiment, in the locked state, the interaction member is rotationally locked with respect to the housing by mechanical cooperation with the resilient member, in particular by means of the spring force provided by the resilient member. In the unlocked state, the interaction member is rotatable with respect to the housing, in particular by mechanical cooperation with the cartridge holder. The resilient member may be secured against rotation with respect to the housing in the locked state and in the unlocked state. According to an embodiment the interaction member is rotationally locked with respect to the housing by mechanical cooperation with the resilient member and when the assembly is switched from the locked state to the unlocked state the resilient member or a further resilient member rotationally biases the interaction member into a second direction opposite to the first direction.

The rotational lock between the interaction member and the resilient member in the locked state may prevent unintentional switching of the assembly from the locked state into the unlocked state. User safety may be increased in this way. In the unlocked state, the interaction member may be easily rotatable with respect to the housing such that the user can immediately realize the assembly being in the unlocked state. Furthermore, in the unlocked state, the interaction member may be configured for separating the cartridge holder from the housing such that the user can realize at once that the cartridge holder is not firmly connected to the housing. This may further help to increase user safety.

According to an embodiment, the assembly provides an axially directed force onto the cartridge holder, in particular onto a cartridge inside the cartridge holder. In this way, in the unlocked state, the cartridge holder may be set apart from the housing. The axially directed force may be provided by the resilient member or by at least one additional spring member.

In the unlocked state, the cartridge holder may be automatically axially separated from the housing due to the axially directed force. This force helps the user to take notice of the unlocked state. An unintentional dose setting or dose delivery operation by the user, who erroneously believes that the cartridge holder is firmly connected to the housing, can be prevented in this way. The user can realize at once, that the assembly is in the unlocked state.

According to an embodiment, the resilient member is configured to provide a radially inwards directed force onto the interaction member. The radially inwards directed force may be great enough to rotationally lock the interaction member and the resilient member such that rotation of the interaction member in the second direction is prevented when the assembly is in the locked state.

Due to the radially inwards directed force, the interaction member may be secured in a defined rotational position with respect to the housing when the assembly is in the locked state. When the assembly is in the unlocked state, the radially inwards directed force may not have a corresponding effect onto the interaction member such that, in the unlocked state, rotational lock between the resilient member and the interaction member may be prevented. Thus, the interaction member may be freely moveable in the unlocked state.

According to an embodiment, for switching from the locked state into the unlocked state, the cartridge holder is rotated in the second direction. The second direction may be opposite to the first direction. The rotational force provided on the cartridge holder may thereby be greater than a rotational counter force provided onto the interaction member by means of the resilient member. In this way, said counterforce may be overcome and the rotational lock between the interaction member and the resilient member may be released.

According to an embodiment, the resilient member comprises at least one snap feature. The snap feature may be part of or may be integrally formed with the resilient member, in particular with a resilient spring arm of the resilient member. Said spring arm may be radially resilient. The snap feature may comprise a protrusion, e.g. a bump. The interaction member may comprise at least one corresponding interaction snap feature. The interaction snap feature may be part of or may be integrally formed with the interaction member. The interaction snap feature may comprise a protrusion, e.g. a bump. The interaction snap feature may be arranged on an outer surface of the interaction member. In the locked state, the snap feature and the interaction snap feature may be configured to abut.

Abutment of the snap feature and the interaction snap feature may rotationally lock the interaction member and the resilient member in the locked state. In the unlocked state, the snap feature and the interaction snap feature may be separated, e.g. angularly separated, from one another such that mechanical interaction of the snap feature and the interaction snap feature for rotationally locking the interaction member and the resilient member may be prevented. When the assembly is switched from the unlocked state into the locked state and vice versa, mechanical cooperation of the snap feature and the interaction snap feature may lead to the rotational force tending to bias the interaction member in a specific rotational direction, e.g. the first direction when the assembly is switched from the locked state into the unlocked state and the second direction when the assembly is switched from the unlocked state into the locked state.

According to an embodiment, in the locked state of the assembly, axial movement of the cartridge holder with respect to the housing is prevented. Axial movement may be prevented by mechanical cooperation of a first fastening means of the cartridge holder and a second fastening means of the housing.

In this way, a firm connection of the cartridge holder and the housing may be enabled when the assembly is in the locked state. In particular, any unintentional movement of the cartridge holder in the locked state may be prevented.

According to an embodiment, mechanical cooperation of the first fastening means and the second fastening means is configured to limit the rotation of the cartridge holder in the first and in the second direction with respect to the housing.

The first and the second fastening means may be configured such that rotation of the cartridge holder in the first direction may be prevented when the assembly is in the locked state. Rotation of the cartridge holder in the second direction may be counteracted when the assembly is in the locked state by the rotational force exerted on the interaction member by the resilient member.

In the unlocked state, the first and the second fastening means may be configured such that rotation of the cartridge holder in the first and in the second direction is, at least in a limited fashion, enabled. Accordingly, in the unlocked state, the user may rotate the cartridge holder in any of the first and the second direction, thereby realizing that the cartridge holder is not firmly connected to the housing.

According to an embodiment, the first and the second fastening means are configured such that axial movement of the cartridge holder with respect to the housing is allowed when the assembly is switched from the locked state into the unlocked state.

Accordingly, the cartridge holder may be, at least in a limited fashion, axially moveable with respect to the housing when the assembly is in the unlocked state.

According to an embodiment, the interaction member comprises at least one first coupling member. The first coupling member may be adapted and arranged for engagement with at least one corresponding second coupling member of the cartridge holder for rotationally locking the interaction member and the cartridge holder.

The first and the second coupling member may mechanically interact for switching the assembly between the locked state and the unlocked state. Furthermore, the first and the second coupling member may mechanically interact when the assembly is in the locked state. In the unlocked state, the first and the second coupling member may mechanically interact only in a limited fashion, e.g. for switching the assembly from the unlocked state into the locked state.

According to an embodiment, the interaction member is secured against axial movement with respect to the housing. The interaction member may comprise a ring-like shape. The resilient member may be at least in parts circumferentially arranged on at least a part of the exterior of the interaction member. Alternatively, the resilient member may be arranged circumferentially on at least a part of the interior of the interaction member. The resilient member may also comprise a ring-like shape.

A further aspect relates to a drug delivery device. The device may comprise the previously described assembly. The device may comprise a cartridge. The cartridge may be, preferably releasably, retained in the cartridge holder. The cartridge may comprise a drug, preferably a plurality of doses of the drug. The device may be a pen-type device, e.g. a pen-type injector.

When the assembly is in the unlocked state, the cartridge holder and, thus, the cartridge is not firmly connected to the housing of the device. In this way, a dose setting and a dose delivery operation of the device, which could lead to the dispense of a dose which does not mach the desired dose, in particular to underdosing, may be prevented when the assembly is in the unlocked state. This may help to facilitate provision of a device having increased dose accuracy and thus, increased user safety.

Of course, features described above in connection with different aspects and embodiments may be combined with each other and with features described below.

Further features and refinements become apparent from the following description of the exemplary embodiments in connection with the accompanying figures.

BRIEF DESCRIPTION OF THE FIGURES

FIG. 12 shows a cross-section of an embodiment of the drug delivery device.

DETAILED DESCRIPTION

Figure 1:
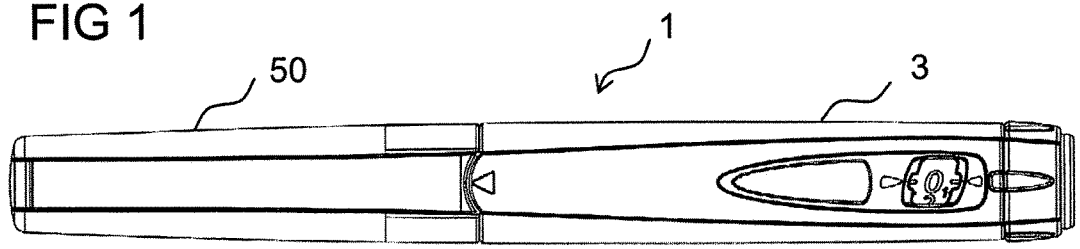
FIG. 1 shows an embodiment of a drug delivery device.
Figure 1:
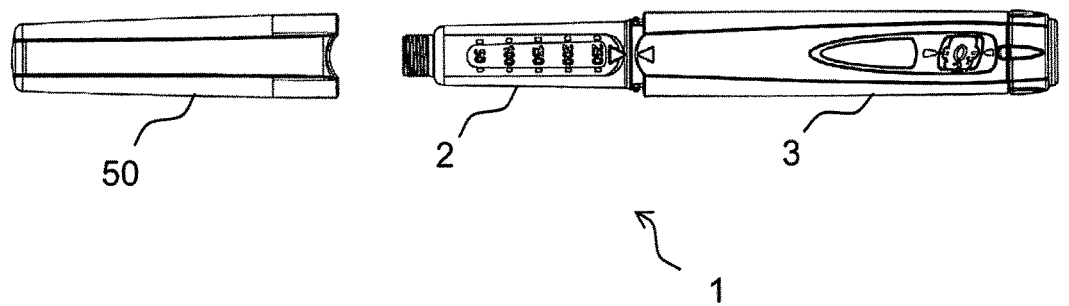

FIG. 1 shows an embodiment of a drug delivery device 1. The drug delivery device 1 is a pen-type device, in particular a pen-type injector. The drug delivery device comprises a housing 3. The drug delivery device 1 comprises a cartridge holder 2.

The drug delivery device 1 and the housing 3 have a distal end and a proximal end. The distal end is indicated by arrow 20 (see FIG. 12). The term "distal end" designates that end of the drug delivery device 1 or a component thereof which is or is to be arranged closest to a dispensing end of the drug delivery device 1. The proximal end is indicated by arrow 30 (see FIG. 12). The term "proximal end" designates that end of the device 1 or a component thereof which is or is to be arranged furthest away from the dispensing end of the device 1. The distal end 20 and the proximal end 30 are spaced apart from one another in the direction of an axis. The axis may be the longitudinal axis of the device 1.

The device 1 is a reusable device, i.e. it is configured for setting and dispensing a plurality of doses of a drug. The drug may be a fluid drug. The term "drug", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36[Asp28] Exendin-4(1-39),
des Pro36[IsoAsp28] Exendin-4(1-39),
des Pro36[Met(O)14, Asp28] Exendin-4(1-39), des Pro36[Met(O)14, IsoAsp28] Exendin-4(1-39),
des Pro36[Trp(O2)25, Asp28] Exendin-4(1-39),
des Pro36[Trp(O2)25, IsoAsp28] Exendin-4(1-39),
des Pro36[Met(O)14 Trp(O2)25, Asp28] Exendin-4(1-39),
des Pro36[Met(O)14 Trp(O2)25, IsoAsp28] Exendin-4(1-39); or
des Pro36[Asp28] Exendin-4(1-39),
des Pro36[IsoAsp28] Exendin-4(1-39),
des Pro36[Met(O)14, Asp28] Exendin-4(1-39),
des Pro36[Met(O)14, IsoAsp28] Exendin-4(1-39),
des Pro36[Trp(O2)25, Asp28] Exendin-4(1-39),
des Pro36[Trp(O2)25, IsoAsp28] Exendin-4(1-39),
des Pro36[Met(O)14 Trp(O2)25, Asp28] Exendin-4(1-39),
des Pro36[Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36[Asp28] Exendin-4(1-39)-Lys6-NH2,
des Asp28 Pro36, Pro37, Pro38Exendin-4(1-39)-NH2,
H-(Lys)6-des Pro36, Pro38[Asp28] Exendin-4(1-39)-NH2,
H-Asn-(Glu)5des Pro36, Pro37, Pro38[Asp28] Exendin-4(1-39)-NH2, des Pro36, Pro37, Pro38[Asp28] Exendin-4(1-39)-(Lys)6-NH2, H-(Lys)6-des Pro36, Pro37, Pro38[Asp28] Exendin-4(1-39)-(Lys)6-NH2, H-Asn-(Glu)5-des Pro36, Pro37, Pro38[Asp28] Exendin-4(1-39)-(Lys)6-NH2,
H-(Lys)6-des Pro36[Trp(O2)25, Asp28] Exendin-4(1-39)-Lys6-NH2, H-des Asp28 Pro36, Pro37, Pro38[Trp(O2)25] Exendin-4(1-39)-NH2, H-(Lys)6-des Pro36, Pro37, Pro38[Trp(O2)25, Asp28] Exendin-4(1-39)-NH2, H-Asn-(Glu)5-des Pro36, Pro37, Pro38[Trp(O2)25, Asp28] Exendin-4(1-39)-NH2, des Pro36, Pro37, Pro38[Trp(O2)25, Asp28] Exendin-4(1-39)-(Lys)6-NH2, H-(Lys)6-des Pro36, Pro37, Pro38[Trp(O2)25, Asp28] Exendin-4(1-39)-(Lys)6-NH2, H-Asn-(Glu)5-des Pro36, Pro37, Pro38[Trp(O2)25, Asp28] Exendin-4(1-39)-(Lys)6-NH2, H-(Lys)6-des Pro36[Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38[Met(O)14, Asp28] Exendin-4(1-39)-NH2, H-Asn-(Glu)5-des Pro36, Pro37, Pro38[Met(O)14, Asp28] Exendin-4(1-39)-NH2, des Pro36, Pro37, Pro38[Met(O)14, Asp28] Exendin-4(1-39)-(Lys)6-NH2, H-(Lys)6-des Pro36, Pro37, Pro38[Met(O)14, Asp28] Exendin-4(1-39)-(Lys)6-NH2, H-Asn-(Glu)5 des Pro36, Pro37, Pro38[Met(O)14, Asp28] Exendin-4(1-39)-(Lys)6-NH2, H-Lys6-des Pro36[Met(O)14, Trp(O2)25, Asp28] Exendin-4(1-39)-Lys6-NH2, H-des Asp28 Pro36, Pro37, Pro38[Met(O)14, Trp(O2)25] Exendin-4(1-39)-NH2, H-(Lys)6-des Pro36, Pro37, Pro38[Met(O)14, Asp28] Exendin-4(1-39)-NH2, H-Asn-(Glu)5-des Pro36, Pro37, Pro38[Met(O)14, Trp(O2)25, Asp28] Exendin-4(1-39)-NH2, des Pro36, Pro37, Pro38[Met(O)14, Trp(O2)25, Asp28] Exendin-4(1-39)-(Lys)6-NH2, H-(Lys)6-des Pro36, Pro37, Pro38[Met(O)14, Trp(O2)25, Asp28] Exendin-4(S1-39)-(Lys)6-NH2,
H-Asn-(Glu)5-des Pro36, Pro37, Pro38[Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A protective cap 50 can be slid over the cartridge holder 2 of the device 1. The protective cap 50 covers at least a part of the cartridge holder 2 for protecting the cartridge holder 2 from environmental influences.

Figure 2:
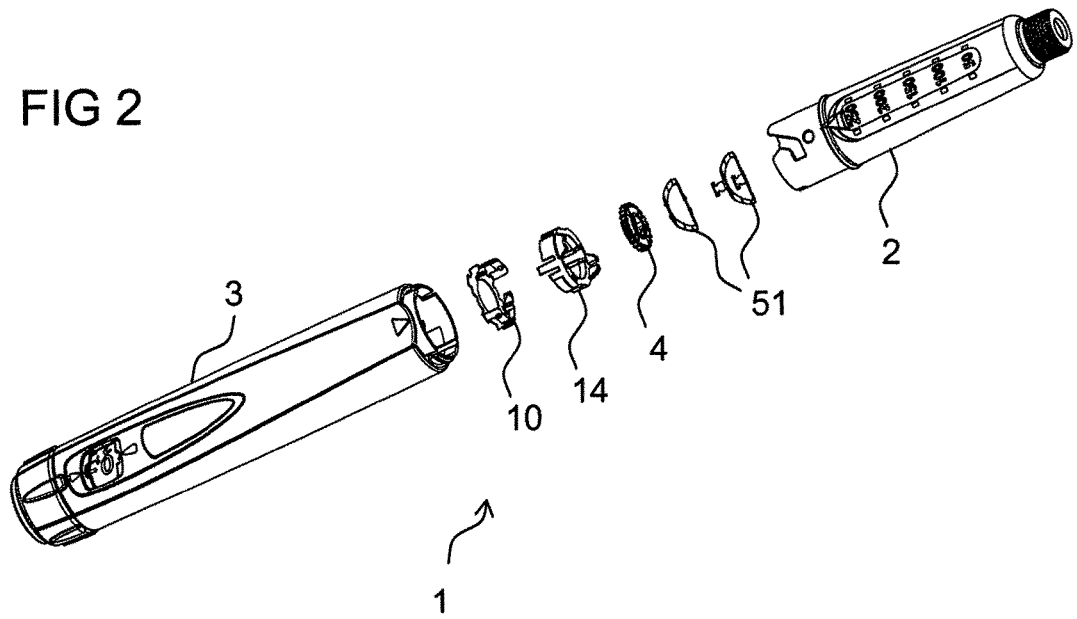
FIG. 2 shows a perspective view of several parts of the drug delivery device of FIG. 1.

FIG. 2 shows a perspective view of several parts of the drug delivery device 1 according to FIG. 1.

The device comprises a resilient member 10. The device 1 comprises an interaction member 14. The resilient member 10 and the interaction member 14 are hollow or ring-shaped members. The resilient member 10 and the interaction member 14 encompass a guide nut 4 when assembled within the housing 3 of the device 1, which is described later on in more detail.

The drug delivery device 1 comprises two spring members 51. Alternatively, the device 1 can comprise only one spring member 51, or even more spring members 51, i.e. three or four spring members 51. The spring members 51 comprise disc springs. In an assembled state of the device 1, the spring members 51 are arranged between the interaction member 14 and the cartridge 6 inside the cartridge holder 2. The spring members 51 are coupled to one another. Accordingly, axial and rotational movement of one spring member 51 relative to the other spring member 51 is prevented. The spring member 51 which is arranged closer to the interaction member 14 is secured against movement with respect to the interaction member 14 by mechanical cooperation with a locking feature 12 of the interaction member 14 (see FIG. 3). According to this embodiment, the spring members 51 comprise a separate component of the device 1. Alternatively, the spring members 51 can be part of or can be integrally formed with the resilient member 10, for example.

Furthermore, the spring members 51 exert a distally directed force onto the cartridge holder 2 such that, when the cartridge holder 2 is not firmly connected, i.e. secured against axial and rotational movement, to the housing 3, the cartridge holder 2 is pushed away from the housing 3. Said functionality of the spring members 51 is explained in connection with the operation for connecting the cartridge holder 2 to the housing 3 as describe below.

Furthermore, the spring members 51 exert a distally directed force onto the cartridge holder 2 such that, when the cartridge holder 2 in not firmly connected, i.e. secured against axial and rotational movement, to the housing 3, the cartridge holder 2 is pushed away from the housing 3. Said functionality of the spring members 51 is explained in connection with the operation for connecting the cartridge holder 2 to the housing 3 as describe below.

Figure 3:
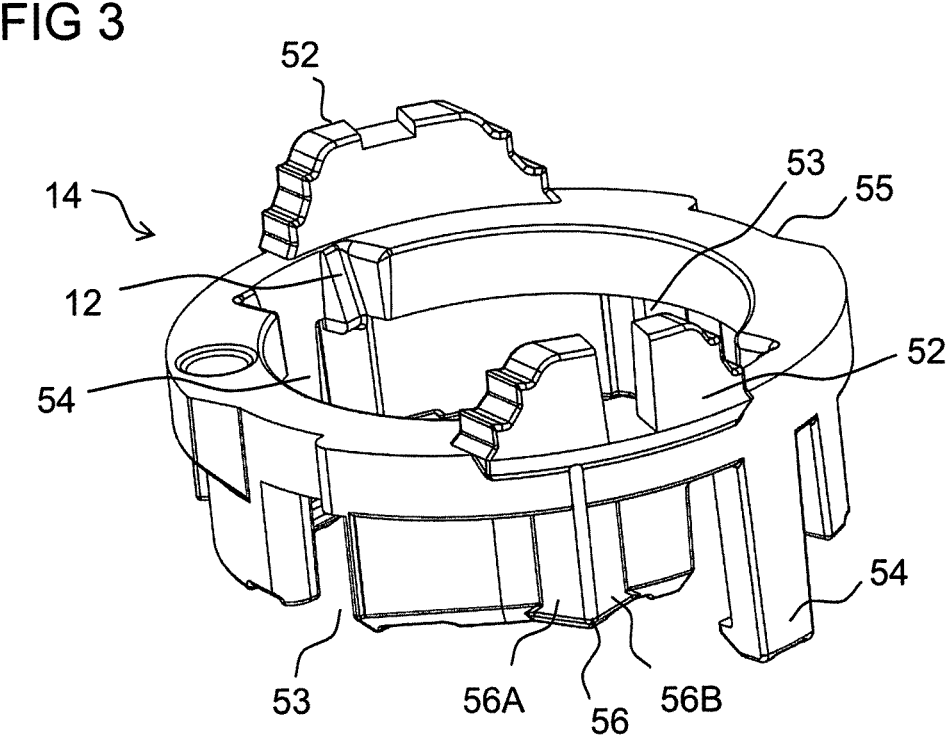
FIG. 3 shows a perspective view of an interaction member of the drug delivery device.

FIG. 3 shows a perspective view of the interaction member 14.

The interaction member 14 is a ring-shaped member. The interaction member 14 is assembled within the housing 3 such that it is rotatable with respect to the longitudinal axis of the device 1. In an unlocked state of the device 1, i.e. when the cartridge holder 2 is not firmly connected to the housing 3, the interaction member 14 is rotatable between a first and a second position. When the device 1 is in a locked state, i.e. when the cartridge holder 2 is firmly connected to the housing 3, the interaction member 14 is in the first position, the interaction member 14 being secured against rotation with respect to the housing 3 by mechanical cooperation with the resilient member 10 which is explained later in detail.

The interaction member 14 provides retaining means 54. The retaining means 54 are arranged on opposite sides of the ring-shaped body of the interaction member 14. The retaining means retains the interaction member 14 within the housing 3 and prevents axial movement of the interaction member 14 with respect to the housing 3.

In the embodiment shown, the interaction member 14 comprises radial recesses 53. The recesses 53 are arranged on opposite sides of the main body of the interaction member 14. Thus, the interaction member 14 is a hollow member, not only in axial direction, but also in radial direction with respect to the housing 3. The recesses 53 enable a locking means 9 (see FIG. 5) of the resilient member 10 to pass the radial recesses 53 towards the center of the interaction member 14 in order to engage with the guide nut 4. In a further embodiment, the locking means 9 are located on the inner side of the interaction member 14 (not explicitly shown). In this case, the radial recesses 53 may be redundant and the locking means 9 could be moveable via a ramp on the interaction member 14 for engaging with the guide nut 4. Engagement of the locking means 9 and the guide nut 4 is explained below in detail.

The interaction member 14 comprises a ramp-shaped exterior surface. Said surface comprises two ramps 55. The ramps 55 are arranged at opposite sides of the exterior of the interaction member 14. The ramps 55 are angled ramps providing a transition from a broader diameter to a narrowed diameter of the exterior of the interaction member 14. The ramps 55 are arranged substantially at the positions of the corresponding radial recesses 53. The ramps 55 are designed in order to enable the previously mentioned locking means 9 of the resilient member 10 to slide along the exterior surface of the interaction member 14 from the broader part to the narrowed part and to perform a radial movement towards the center of the interaction member 14 when reaching the narrowed diameter of the interaction member 14. Interaction between the interaction member 14 and the locking means 9 is explained in greater detail in connection with FIG. 6.

The interaction member 14 comprises an interaction snap feature 56. The interaction snap feature 56 may interact with a corresponding snap feature 60 (see FIG. 5) of the resilient member 10 for rotationally locking the interaction member 14 in the first position with respect to the housing 3. The interaction snap feature 56 is wedge-shaped. The interaction snap feature 56 comprises a bump. The interaction snap feature 56 is arranged on the outer surface of the interaction member 14.

The interaction member 14 comprises first coupling members 52. The first coupling members 52 are arranged on opposite sides at the top of the ring-shaped body of the interaction member 14. The first coupling members 52 are formed trapezoidal and protrude in the distal direction from the interaction member 14.

Figure 10:
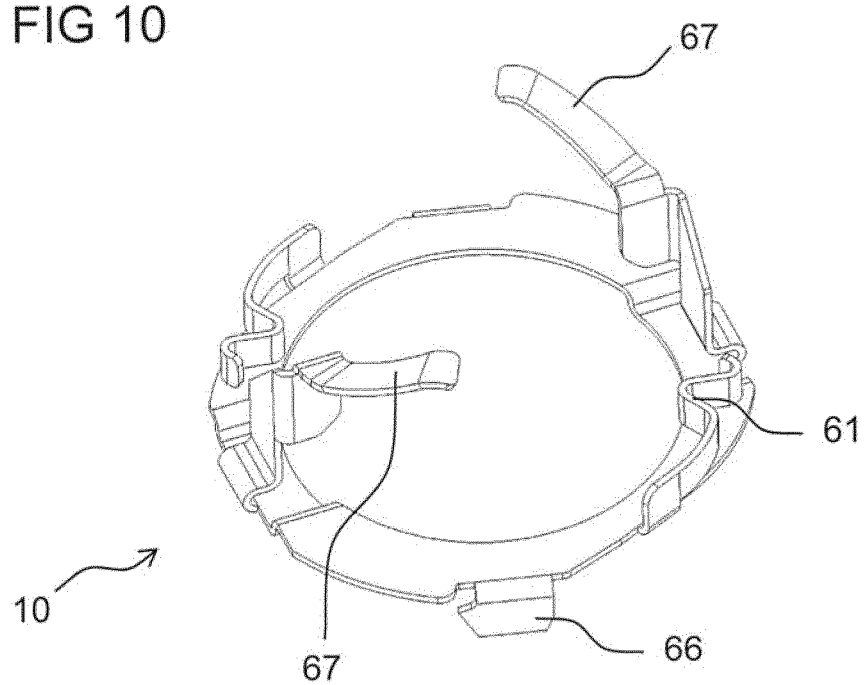
FIG. 10 shows a perspective view of a resilient member of the drug delivery device according to a further embodiment.

The first coupling members 52 are provided for interaction and engagement with corresponding second coupling members 63 (see FIGS. 7 and 10) of the cartridge holder 2. When the first coupling members 52 mechanically cooperate with the second coupling members 63, the interaction member 14 is rotationally locked to the cartridge holder 2. The interaction member 14 can be operated, e.g. rotated, by mechanical cooperation of the first and second coupling members 52, 63. The interaction member 14 is rotatable during a mounting movement of the cartridge holder 2, when said cartridge holder 2 is assembled to the housing 3, i.e. when switching the device 1 from the unlocked state into the locked state, as explained in connection with FIG. 7.

Figure 4:
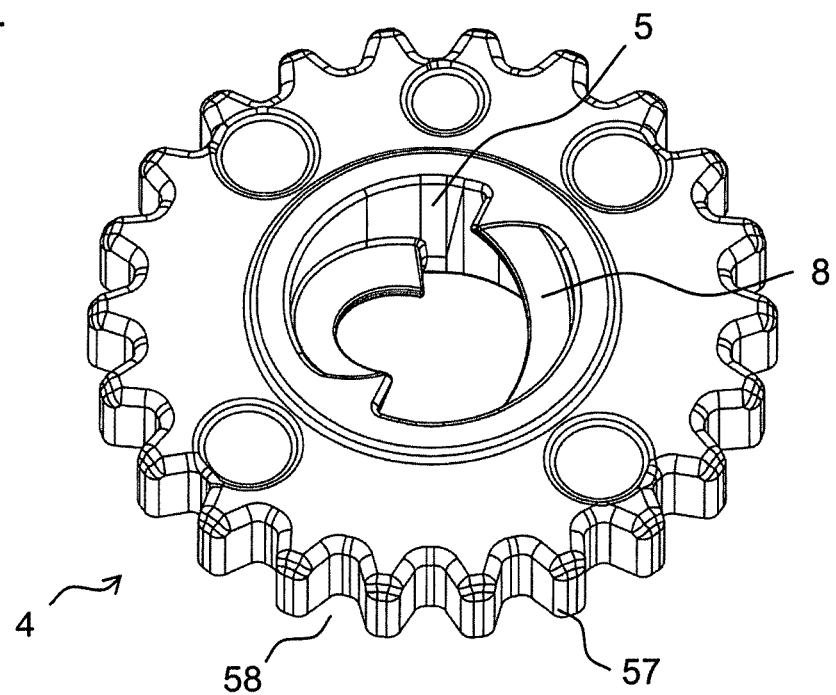
FIG. 4 shows a perspective view of a guide nut of the drug delivery device.

FIG. 4 shows a perspective view of a guide nut 4.

The guide nut 4 comprises a centered hole 5. Within the centered hole 5 a screw thread 8 is designed. The screw thread 8 is used for being coupled to a piston rod 17 (see FIG. 12) in order to urge the piston rod 17 in a predetermined helical movement as explained in greater detail in connection with FIG. 12. The guide nut 4 comprises a toothed wheel. The guide nut 4 comprises teeth 57 and notches 58 on the exterior circumference of the guide nut 4. The teeth 57 may be designed as spikes. The notches 58 may be designed as interspaces between the teeth 57 or spikes. The guide nut 4 may be rotationally arranged within the housing 3 of the device 1. In one state of the device 1, in particular in the locked state, the guide nut 4 is rotationally fixed by the locking means 9 of the resilient member 10 as explained in connection with FIG. 6. In another state, preferably in the unlocked state during which a resetting operation can be performed, the guide nut 4 is rotatable with respect to the housing 3. The interaction member 14, according to FIG. 3, may act as an actuation means in order to enable a switching between the locked state and the unlocked state.

Figure 5:
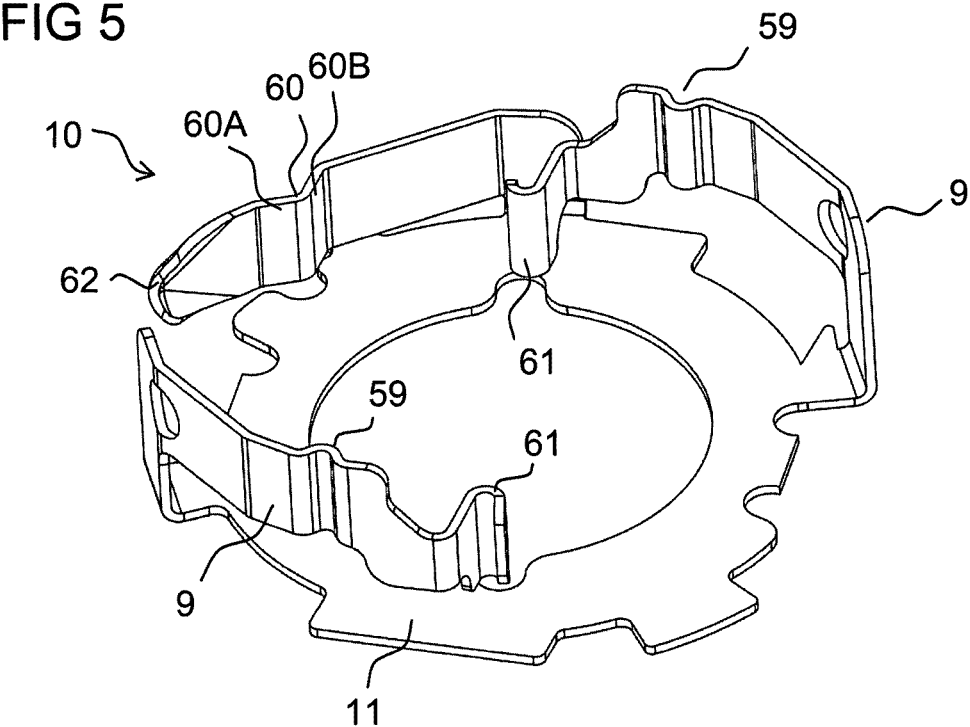
FIG. 5 shows a perspective view of a resilient member of the drug delivery device.

FIG. 5 shows the resilient member 10.

The resilient member 10 is secured against rotational movement with respect to the housing 3, e.g. by mechanical cooperation of retaining members 66 (see FIG. 10) with corresponding retaining members, e.g. nuts, of the housing 3 (not explicitly shown in the Figures). The resilient member 10 comprises a ring-shaped carrier 11. The resilient member 10 comprises the previously mentioned locking means 9. The locking means 9 is formed in the carrier 11. The locking means 9 comprises at least one spring arm. In this embodiment, the locking means 9 comprises two arms or cantilevers which are arranged on opposite sides of the carrier 11.

Alternatively, the locking means 9 could comprise three or more spring arms. With one end, the locking means 9 are fixed to the carrier 11 and with the other end the locking means 9 are free. At a respective free end, the respective locking means 9 comprises an edge or a hook 61 for engagement with corresponding notches 58 or interspaces of the guide nut 4. The locking means 9 are resiliently mounted on the carrier 11. Thus, the locking means 9 are pivotable on their free ends with the hooks 61 thereon towards the centre of the carrier 11. Thus, the locking means 9 may perform a radial movement.

The locking means 9 provide protrusions 59. The protrusions 59 are molded on the cantilever-formed locking means 9. The protrusions 59 are directed towards the centre of the carrier 11. The protrusions 59 are designed for sliding along the ramps 55 on the exterior of the interaction member 14 (see FIG. 3). For further details see FIG. 6.

The resilient member 10 provides a retaining means 62. The retaining means 62 may comprise a further spring arm. In particular, the retaining means 62 may be formed as another cantilever-structure. The retaining means 62 comprises a fixed end on the carrier 11 and a free end pointing substantially in a tangential direction with respect to the ring-shaped carrier 11. The retaining means 62 comprises the previously mentioned snap feature 60. The snap feature 60 mechanically interacts with the wedge-shaped interaction snap feature 56 of the interaction member 14 in order to hold the interaction member 14 in a fixed, in particular rotationally secured position, with respect to the resilient member 10 when the device 1 is in the locked state.

The retaining means 62 is biased in the radial inward direction with respect to the longitudinal axis of the device 1. In particular, the retaining means 62 is configured to exert a radially inwards directed force onto the interaction member 14. Said force must be overcome for rotating the interaction member 14 into the first position, in particular for rotationally locking the interaction member 14 and the resilient member 10 by abutment of the snap features 56, 60. Accordingly, in the locked state of the device 1, the radially inwards directed force must be overcome for releasing the rotational lock between the interaction member 14 and the resilient member 10 and for rotating the interaction member 14 out of the first position. This is explained later on in detail.

Figure 6:
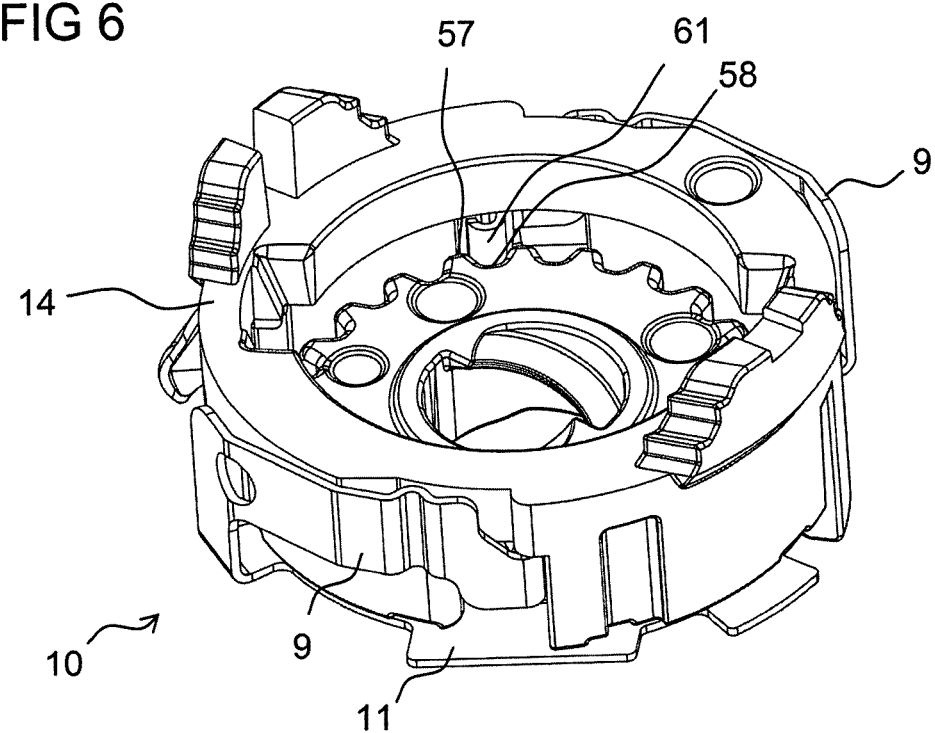
FIG. 6 shows a perspective view of an assembled interaction member, guide nut and resilient member according to FIGS. 3 to 5.

FIG. 6 shows an assembly of the interaction member 14, the resilient member 10 and the guide nut 4.

The guide nut 4 is encompassed by the interaction member 14 and the resilient member 10. The interaction member 14 provides a ledge on the inner circumference of the ring-shaped body in order to hold the guide nut 4 within the interaction member 14 and to prevent upward movement of the guide nut 4 out of the ring-shaped body of the interaction member 14. The guide nut 4 is securely embedded between the interaction member 14 and the carrier 11 of the resilient member 10. The guide nut 4 may be prevented from axial movement with respect to the housing 3 by means of a web 32 of the housing 3 which is explained in detail in connection with FIG. 12.

Furthermore, the locking means 9 of the resilient member 10 are circumferentially arranged on at least a part of the exterior of the interaction member 14. Thereby, the protrusions 59 (see also FIG. 5) of the cantilever-formed locking means 9 are directed towards the exterior surface of the interaction member 14. This may have the effect that the locking means 9 can slide via the protrusions 59 along the ramps 55 on the exterior of the interaction member 14.

FIG. 6 shows a position of the interaction member 14 representing an engaged state of the locking means 9. The locking means 9 have passed with their free ends the radial recesses 53 of the interaction member 14 as explained in connection with of FIG. 3. This is enabled due to the fact that the protrusions 59 are lying on the narrowed part of the diameter of the interaction member 14.

In FIG. 6, the locking means 9 engage via their hooks 61 with the guide nut 4. In particular, the hooks 61 rest between the teeth 57 in respective notches 58. Moreover, in this position, the hooks 61 engage behind a corresponding edge of the radial recesses 53 of the interaction member 14. This has the effect that a radial movement of the hooks 61 out of engagement with the teeth 57 and away from the guide nut 4 due to torsional moments is prevented in order to enable a secure engagement between the locking means 9 and the guide nut 4. Torsional moments may, for example, occur during interaction with the guide nut 4 and a piston rod 17 guided by the guide nut 4 during drug delivery or while trying to inject a dose but having a bent needle.

In FIG. 6, rotational movement of the guide nut 4 with respect to the resilient member 10 is prevented. In other words, the guide nut 4 is rotationally fixed with respect to the resilient member 10. Since the resilient member 10 is arranged within the housing 3 in a rotationally fixed manner, the guide nut 4 is also rotationally fixed with respect to the housing 3. In this position, which preferably may be taken during drug delivery, the guide nut 4 urges the piston rod to perform a predetermined movement, i.e. a helical movement, the piston rod 17 thereby being threaded through the inner screw thread 8 of the guide nut 4 (see FIG. 4).

In case the interaction member 14 is rotated counter clockwise, i.e. in the direction the cartridge holder 2 is rotated for being released from the device 1, i.e. for switching the device 1 in the unlocked state, the protrusions 59 of the locking means 9 slide along the angled ramp 55 of the interaction member 14 from the narrowed part to the broader part of the diameter of the interaction member 14. Hence, the locking means 9, in particular the hooks 61, are urged out of engagement with the notches 58 of the guide nut 4, the locking means 9 pivoting in radial direction away from the centre of the assembly. Thus, by rotating the interaction member 14, the locking means 9 is released out of engagement with the guide nut 4. This may allow the guide nut 4 to rotate with respect to the resilient member 10. When the guide nut 4 is allowed to rotate with respect to the housing 3, the device 1 is in the unlocked state. When the guide nut 4 is allowed to rotate with respect to the housing 3, a reset operation of the piston rod 17 being coupled with the guide nut 4 may be started. This means, the piston rod 17 may be shifted in proximal direction.

Figure 7:
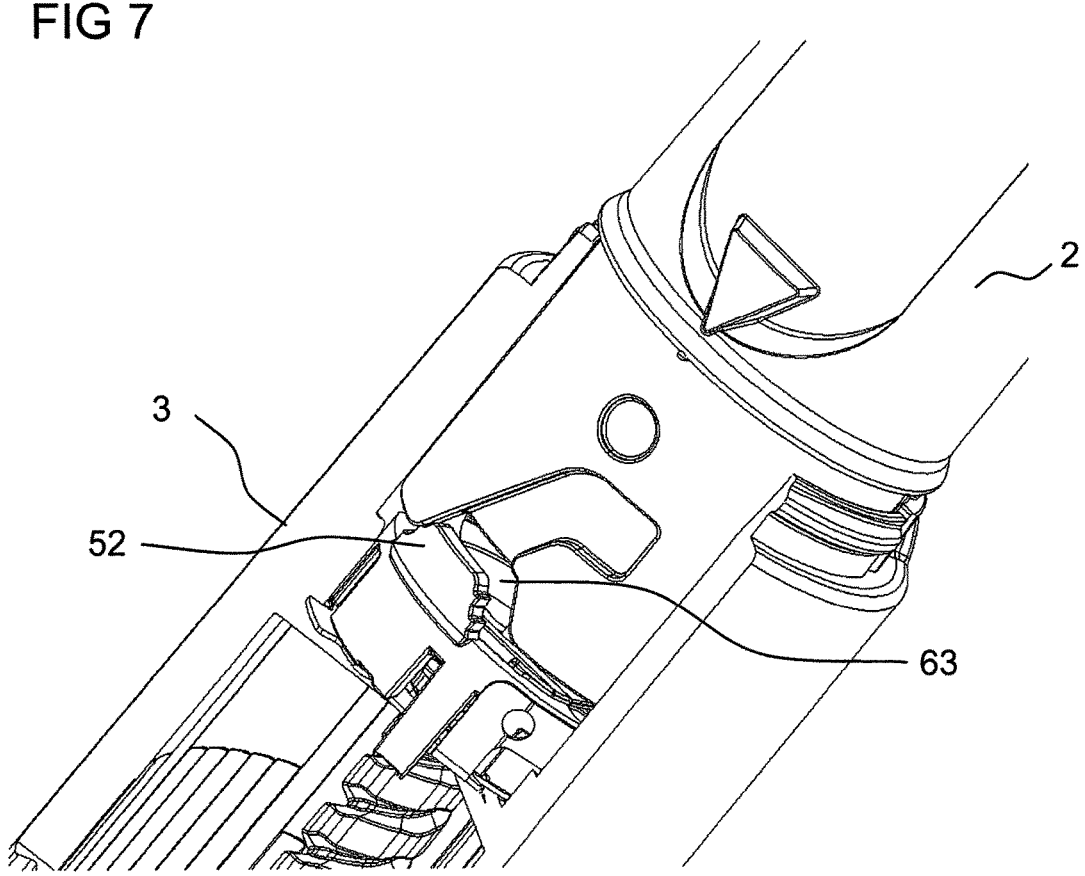
FIG. 7 shows a perspective view of a part of the drug delivery device with a cartridge holder being partially inserted into the housing.

FIG. 7 shows a perspective view of a part of the drug delivery device 1 with the cartridge holder 2 being partially inserted into the housing 3. FIG. 7, furthermore, shows the assembly of the interaction member 14 and the resilient member 10 according to FIG. 6, arranged within the housing 3.

In FIG. 7, the interaction member 14 is in a position, wherein the locking means 9 is disengaged from the guide nut 4 as explained in connection with FIG. 6.

With respect to FIG. 7, the cartridge holder 2 is further moved into the housing 3 such that the first coupling member 52 of the interaction member 14 and the second coupling member 63 of the cartridge holder 2 interact and engage with each other. This effects a rotational movement of the interaction member 14 caused by a rotational movement of the cartridge holder 2 during mounting the cartridge holder 2 within the housing 3. Thus, the cartridge holder 2 operates the interaction member 14 in order to switch the device 1 from the unlocked state to the locked state as depicted in FIG. 6 with the interaction member 14 acting as an intermediary between the cartridge holder 2 and the locking means 9. This is explained in connection with FIGS. 8 and 9 in more detail.

By mounting the cartridge holder 2 with the housing 3, engagement of the locking means 9 of the resilient member 10 with the guide nut 4 is enabled. Due to the engagement of the interaction member 14 with the cartridge holder 2, the interaction member 14 is switched from the second position with respect to the housing 3 into the first position with respect to the housing 3 where it is rotationally locked to the resilient member 10 wherein the first and second positions represent discrete and stable positions. Hence, the mechanism of rotationally fixing the guide nut 4 within the housing 3 as explained above is established in a secure and easy manner in order to prepare the drug delivery device 1 for drug delivery.

Figure 8:
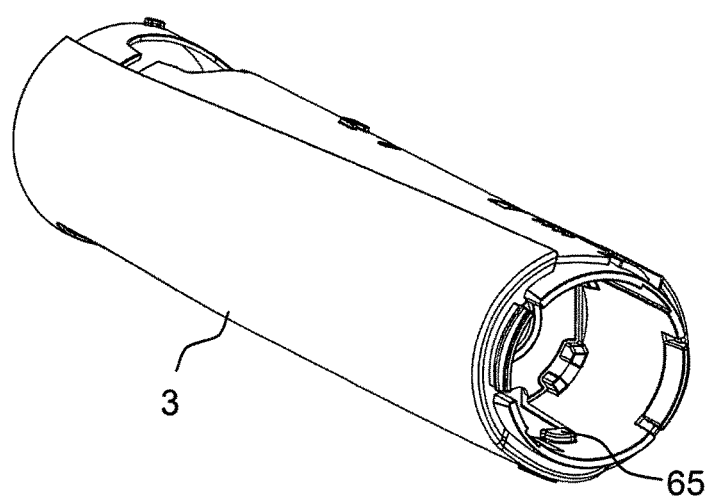
FIG. 8 shows a perspective view of the housing of the drug delivery device.
Figure 9:
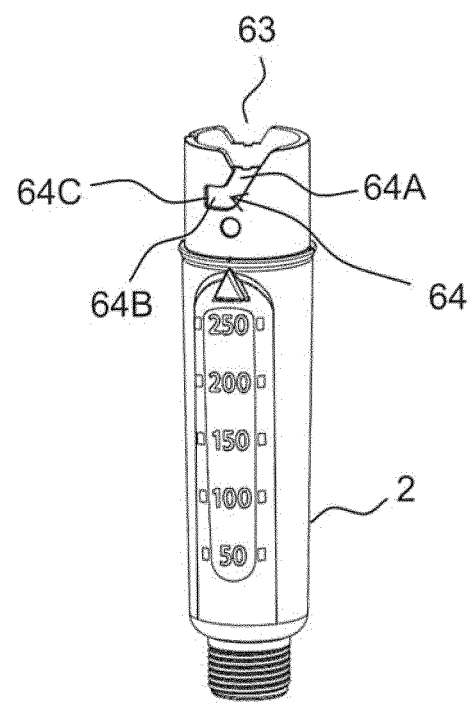
FIG. 9 shows a perspective view of the cartridge holder of the drug delivery device.

FIG. 8 shows the housing 3 of the drug delivery device 1. FIG. 9 shows the cartridge holder 2 of the drug delivery device 1.

The cartridge holder 2 is releasably connectable to the housing 3 of the drug delivery device 1. The housing 3 comprises two second fastening means 65, wherein only one of the second fastening means 65 is shown in FIG. 8. Alternatively, the housing 3 can comprise only one second fastening means 65 or even more, e.g. three or four second fastening means 65. The second fastening means 65 are arranged in the distal end section of the housing 3, i.e. the end section which is to be connected to the cartridge holder 2. The second fastening means 65 are arranged on the inner surface of the housing 3. The two second fastening means 65 are arranged oppositely with respect to one another.

The second fastening means 65 comprises a pin. The pin protrudes radially inwards from the inner surface of the housing 3. In the embodiment shown in FIG. 8, the angular extent of the second fastening means 65 is greater than its axial extent. However, the situation may be vice versa, as well, i.e. the axial extent of the second fastening means 65 may be greater than its angular extent. Alternatively, the second fastening means 65 can comprise a square or circular shape. The respective second fastening means 65 is adapted to mechanically cooperate with the corresponding first fastening means 64, e.g. a guide track, of the cartridge holder 2 (see FIG. 9).

The cartridge holder 2 comprises two first fastening means 64. Alternatively, the cartridge holder 2 can comprise only one first fastening means 64 or even more, e.g. three or four first fastening means 64. The number of first fastening means 64 corresponds to the number of second fastening means 65. The first fastening means 64 are arranged in the proximal end section of the cartridge holder 2, i.e. the end section which is to be connected to the housing 3. The first fastening means 64 are arranged on the outer surface of the cartridge holder 2. The two first fastening means 64 are arranged oppositely with respect to one another.

The respective first fastening means 64 comprises a first section 64A. The first fastening means 64 comprises a second section 64B. The path defined by the first section 64A encloses an angle with the longitudinal axis of the device 1. The angle which is enclosed by the path defined by the first section 64A with the longitudinal axis amounts to by 45 degrees in the embodiment shown in FIG. 9. However, also other angles are conceivable, e.g. the angle can amount to a minimum value of 10 degrees or a maximum value of 120 degrees. The second section 64B runs less obliquely with respect to the longitudinal axis than the first section 64A. The angle enclosed by the path defined by the first section 64A with the longitudinal axis of the device 1 is smaller than the angle enclosed by the path defined by the second section 64B with the longitudinal axis. The angle which is enclosed by the path defined by the second section 64B with the longitudinal axis amounts to 90 degrees in the embodiments shown in FIG. 9.

The first section 64A and the second section 64B form a continuous guide track. In other words, for connecting or disconnecting the cartridge holder 2 to the housing 3, i.e. for switching the device 1 from the unlocked state into the locked state and vice versa, the second fastening means 65 can pass from the first section 64A directly into the second section 64B and vice versa.

The second section 64B comprises an angular stop face 64C. The angular stop face 64C is formed by a sidewall of the second section 64B. When the second fastening means 65 mechanically cooperates with the angular stop face 64C, further rotation of the cartridge holder 2 with respect to the housing 3 for connecting the cartridge holder 2 and the housing 3 is prevented.

The cartridge holder 2 further comprises two of the previously mentioned second coupling members 63. The second coupling members 63 are arranged in the proximal end section of the cartridge holder 2. The two second coupling members 63 are arranged oppositely with respect to one another. The second coupling members 63 comprise trapezoidal indentations. The respective second coupling member 63 comprises sloped edges. The second coupling member 63 comprises an angular extent which is greater than the angular extent of the first section 64A. The distal end of the respective second coupling member 63 passes over into the proximal end of the first section 64A of the respective first fastening means 64.

In the following, the operation of switching the device 1 from the unlocked state into the locked state, i.e. of firmly connecting the cartridge holder 2 to the housing 3, is described in detail.

For connecting the cartridge holder 2 to the housing 3, the cartridge holder 2 is moved, in particular at least one of axially moved and rotated, with respect to the housing 3. Thereby, the second fastening means 65 is introduced into the respective second coupling member 63. In particular, the cartridge holder 2 is moved with respect to the housing 3 until the second fastening means 65 mechanically cooperates with the second coupling member 63. Upon further movement of the cartridge holder 2 with respect to the housing 3, the second fastening means 65 is brought into mechanical cooperation with the first section 64A. When the second fastening means 65 mechanically cooperates with the first section 64A, the cartridge holder 2 is moved proximally with respect to the housing 3 such that the first section 64A slides along the second fastening means 65. Thereby, the second coupling member 63 is moved towards the first coupling member 52 of the interaction member 14.

Upon axial movement, the cartridge holder 2 is rotated in a first direction, which is in the following referred to as connection direction, with respect to the housing 3 by mechanical cooperation of the first section 64A and the second fastening means 65. The interaction member 14 does not yet rotate with respect to the housing 3 as it is not yet rotationally locked to the cartridge holder 2 by mechanical cooperation of the first and second coupling members 52, 63.

The cartridge holder 2 is rotated by an angle of less than 45 degrees with respect to the housing 3 while the second fastening means 65 mechanically cooperates with the first section 64A. The angle is defined by the angle which the path defined by the first section 64A encloses with the longitudinal axis of the device 1 as described above.

At the distal end of the first section 64A, the first section 64A directly passes over into the second section 64B. When the second fastening means 65 mechanically cooperates with the distal end of the first section 64A, the second coupling member 63 mechanically cooperates with the first coupling member 52, in particular, the first and second coupling members 52, 63 are engaged. Accordingly, as described above, the interaction member 14 is now rotationally locked to the cartridge holder 2.

At the distal end of the first section 64A, the second fastening means 65 is brought into mechanical cooperation with a distal and a proximal wall of the second section 64B such that further axial movement of the cartridge holder 2 with respect to the housing 3 is prevented. In particular, mechanical cooperation of the second fastening means 65 with the distal wall of the second section 64B prevents further proximal movement of the cartridge holder 2 with respect to the housing 3 during the connection operation.

The cartridge holder 2 is now further rotated in the first direction, but no longer axially moved with respect to the housing 3. Thereby, the interaction member 14 is rotated in the first direction, the locking means 9 of the resilient member 10 sliding along the exterior surface of the interaction member 14 from the broader part to the narrowed part as well as the retaining means 62 sliding along the exterior part of the interaction member 14.

The cartridge holder 2 is rotated such that the second section 64B slides along the second fastening means 65 until the second fastening means 65 mechanically cooperates with the angular end stop 64C. The cartridge holder 2 is rotated in the same direction when the second fastening means 65 mechanically cooperates with the first and the second sections 64A, 64B for connecting the cartridge holder 2 to the housing 3, i.e. in the connection direction.

While rotating the cartridge holder 2, and thus, the interaction member 14 further in the first direction, in particular while the angular end stop 64C is rotated towards the second fastening means 65, the snap feature 60 starts to mechanically cooperate with the interaction snap feature 56, in particular the first sloped section 56A of the interaction snap feature 56 (see FIG. 3) mechanically cooperates with the first sloped section 60A of the snap feature 60 (see FIG. 5). Thereby, the retaining means 62 is bowed in the radial outward direction with respect to the housing 3 against the radially inwards directed force provided by the retaining means 62. Due to mechanical cooperation of the sloped sections 56A, 60A, the radially inwards directed force is converted into a tangential, i.e. rotational force, in particular into a rotational force directed into the disconnection direction. The rotational force provided onto the interaction member 14 by means of the rotation of the cartridge holder 2 must be great enough such that said rotational counter force is overcome for the interaction snap feature 56 to pass the snap feature 60 and, hence, for the device 1 to be switched from the unlocked state into the locked state.

When the rotational force provided onto the cartridge holder 2 in the connection direction is greater than the rotational counterforce, the interaction snap feature 56 slides over, i.e. passes, the snap feature 60 such that, once the interaction snap feature 56 has passed the snap feature 60, the retaining means 62 automatically moves back radially inwards and the snap features 56, 60 abut with one another, in particular the second sloped sections 56B, 60B (see FIGS. 3 and 5) of the snap features 56, 60 abut.

Rotation of the interaction member 14 in the direction opposite to the connection direction, which is in the following referred to as disconnection direction, is now prevented by mechanical cooperation of the snap features 56, 60. In particular, the interaction member 14 is rotationally locked to the resilient member 10 by mechanical cooperation of the snap features 56, 60, in particular of the sloped sections 56B, 60B. Now, the interaction member 14 is in a predetermined, i.e. the first, position with respect to the housing 3 such that axial and rotational movement with respect to the housing 3 is prevented. As the interaction member 14 is rotational locked to the cartridge holder 2, rotation of the cartridge holder 2 in the disconnection direction is prevented, as well.

When the interaction member 14 is rotationally locked to the resilient member 10, the second fastening means 65 mechanically cooperates with the angular end stop 64C as described above, further rotation of the cartridge holder 2 in the connection direction thus being prevented, as well. Hence, a rotational force provided onto the interaction member 14 in the connection direction due to mechanical cooperation of the second sloped edges 56B, 60B of the snap features 56, 60 after the interaction snap feature 56 has passed the snap feature 60 cannot lead to further rotational movement of the interaction member 14, and hence, of the cartridge holder 2, in the connection direction. Accordingly, the device 1 is in the locked state, the cartridge holder 2 being firmly connected to the housing 3.

Mechanical cooperation of the second fastening means 65 and the angular end stop 64C can provide an audible or tactile feedback indicating to the user that the cartridge holder 2 is firmly connected to the housing 3. Also, when the interaction snap feature 56 passes the snap feature 60, an audible or tactile feedback can be provided indicating to the user that the interaction member 14 is rotationally locked and, thus, that the cartridge holder 2 is firmly connected to the housing 3.

The second fastening means 65 as well as the first section 64A and the second section 64B comprise a dimension such that the second fastening means 65 mechanically cooperates with the walls of the sections 64A, 64B at any time during the connecting operation. In particular, when the second fastening means 65 mechanically cooperates with the first section 64A, the second fastening means 65 abuts the side walls of the first section 64A. When the second fastening means 65 mechanically cooperates with the second section 64B, it abuts the distal and proximal walls of the second section 64B. As the first and second section 64A, 64B pass over into one another, i.e. the side walls of the first section 64A pass over into the distal and proximal walls of the second section 64B, the second fastening means 65 is at any time in mechanical contact with the wall of one of the sections 64A, 64B during the connection operation.

When the rotational force provided onto the cartridge holder 2 in the connection direction is not greater than the rotational counterforce provided onto the interaction member 14 such that the interaction snap feature 65 does not pass the snap feature 60, the resilient member 10 automatically rotates the interaction member 14 and, hence, the cartridge 2 which is rotationally locked to the interaction member 14, in the disconnection direction, due to the rotational counter force provided onto the interaction member 14. Thereby, the second section 64B of the first fastening means 64 slides back along the second fastening means 65 until reaching the distal end of the first section 64A. Once having reached the distal end of the first section 64A, the cartridge 2 is axially moveable with respect to the housing 3. The previously mentioned spring members 51 now push the cartridge holder 2 in the distal direction, in particular away from the housing 3 and, thus, the first section 64A slides along the second fastening means 65, the cartridge holder 2 thereby being rotated further in the disconnection direction. The coupling means 63 of the cartridge holder 2 is thereby moved out of engagement with the coupling means 52 of the interaction member 14 such that the cartridge holder 2 and the interaction member 14 are no longer rotationally locked with one another.

As an alternative to the spring members 51, the distally directed force may be exerted by the resilient member 10. In this case, the spring members 51 may be redundant and the resilient member 10 may comprise one, preferably two or more, spring arms 67 (see FIG. 10). Said spring arms 67 or cantilevers are arranged on opposite sides of the carrier 11. With one end, the spring arms 67 are fixed to the carrier 11 and with the other end the spring arms 67 are free. The spring arms 67 distally bias the cartridge holder 2, pushing the cartridge holder 2 away from the housing 3 when the cartridge holder 2 is not firmly connected to the housing 3, i.e. when the device 1 is in the unlocked state.

In an alternative embodiment (see FIG. 11), an additional resilient member, e.g. a torsion spring 68, is provided. Said torsion spring 68 is used for rotationally biasing the interaction member 14. In this case, a rotational bias provided on the interaction member 14 by means of the resilient member 10 may be redundant and the resilient member 10 may be provided only for rotationally locking the interaction member 14 and the guide nut 4, for example. The torsion spring 68 rotationally may bias the interaction member 14 in the disconnection direction. Accordingly, the torsion spring 68 automatically rotates the interaction member 14, and hence, the cartridge holder 2, in the disconnection direction when the rotational force provided on the cartridge holder 2 in the connection direction for connecting the cartridge holder 2 to the housing 3 is not great enough for rotationally locking the interaction member 14 to the resilient member 10.

Figure 11:
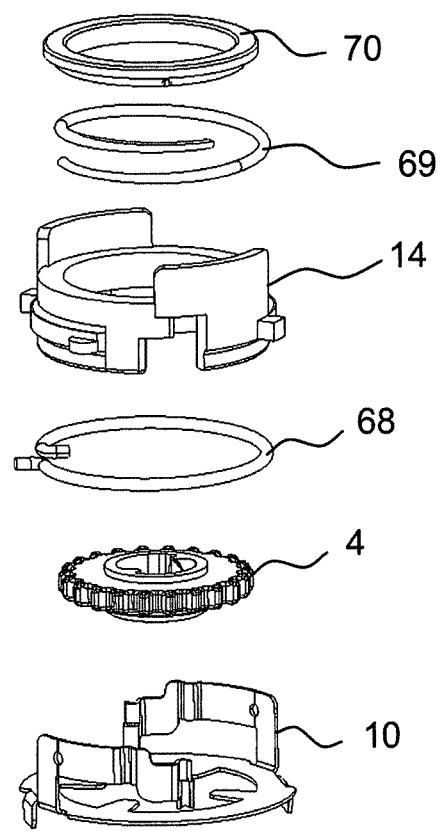
FIG. 11 shows a perspective view of several parts of the drug delivery device of FIG. 1 according to a further embodiment.

In the embodiment shown in FIG. 11, a further spring element 69, e.g. a coil spring, is provided. Said spring element 69 is provided for exerting the previously described distally directed force onto the cartridge holder 2. Hence, in said embodiment, the previously described spring members 51 are redundant, as well. The spring element 69 is covered by a cover 70. Said cover 70 is used for preventing damage to the cartridge holder 2 or to the cartridge 6 when the spring element 69 mechanically cooperates with the proximal end of the cartridge holder 2 or the cartridge 6 for biasing the cartridge holder 2 and the cartridge 6 distally. The cover 70 is arranged between the spring element 60 and the cartridge holder 2.

The previously described automatic rotation of the interaction member 14 in the disconnection direction automatically holds the device 1 into the unlocked state, i.e. the state where the cartridge holder 2 is not firmly connected to the device 1, in particular where the cartridge holder 2 is at least one of axially and rotationally moveable with respect to the device 1, when the force provided onto the cartridge holder 2 is not sufficient for overcoming the rotational counter force provided onto the interaction member 14.

In the following, the operation of switching the device 1 from the locked state into the unlocked state, i.e. of disconnecting the cartridge holder 2 to the housing 3, is described in detail.

For disconnecting the cartridge holder 2 from the housing 3, a rotational force is provided onto the cartridge holder 2, the force being directed into the disconnection direction. Thereby, the retaining means 62 is bowed again in the radial outward direction with respect to the housing 3 against the radially inwards directed force provide by the retaining means 62. Due to mechanical cooperation of the sloped sections 56B, 60B, the radially inwards directed force results in a tangential, i.e. rotational component, in particular a component directed into the connection direction. The rotational force in the disconnection direction provided onto the interaction member 14 by means of the cartridge holder 2 must be great enough such that said rotational counter force onto the interaction member 14 in the connection direction is overcome for the interaction member 14 to be rotated in the disconnection direction, i.e. for the interaction snap feature 56 to pass the snap feature 60.

When the rotational force provided onto the cartridge holder 2 in the disconnection direction is greater than the rotational counterforce provided by the resilient member 10, the interaction snap feature 56 slides over, i.e. passes, the snap feature 60 such that, once the interaction snap feature 56 has passed the snap feature 60, the retaining means 62 automatically moves back radially inwards and the snap features 56, 60, in particular the first sloped sections 56A, 60A abut with one another. Now, the resilient member 10 rotates the interaction member 14 and, hence, the cartridge holder 2 which is rotationally locked to the interaction member 14, in the disconnection direction, due to the rotational force provided onto the interaction member 14 arising from mechanical cooperation of the first sloped sections 56A, 60A. The further steps of the disconnection operation proceed in accordance with the previously described steps of the connection operation in case that rotation of the cartridge holder 2 in the connection direction is not completely performed, in particular in case that the rotational force provided onto the cartridge holder 2 in the connection direction is smaller than the rotational counter force provided onto the interaction member 14.

The drug delivery device is further described in greater detail with regard to FIG. 12.

FIG. 12 shows a cross-section of an embodiment of the drug delivery device 1.

A piston or bung 7 is arranged in the cartridge 6 to be used to expel the drug. The distal end 20 may be provided with an engaging means 21, which can comprise a screw thread for the application of a needle assembly.

The drug delivery device 1 comprises a dosing mechanism, which includes the previously mentioned piston rod 17. The piston rod 17 has a distal end, which is nearest to the distal end 20 of the housing 3 and engages the bung 7 or a bearing 18 that is arranged between the bung 7 and the piston rod 17 to reduce damages that may be caused by friction. The piston rod 17 is movable in the distal direction, i.e. towards the distal end 20, by means of a drive member 19, the piston rod 17 pushing the bung 7 within the cartridge 6 in the distal direction to expel the drug from the cartridge 6 through the engaging means 21. A first screw thread 15 of the piston rod 17 is formed towards the distal end, and a second screw thread 16 of the piston rod 17 is formed nearer to the proximal end of the piston rod 17. The first screw thread 15 and the second screw thread 16 have opposite senses of rotation in this embodiment. One or both of these screw threads 15, 16 may comprise two or more single screw threads in helical alignment, forming a so-called multi-start thread, which is known per se from other mechanical devices.

The drive member 19 forms a tube through which the piston rod 17 is moved. The drive member 19 is generally cylindrical and provided with a bearing 22 carrying a radially extending flange 23 at the proximal end. The second screw thread 16 of the piston rod 17 is coupled with a corresponding screw thread on the inner wall of the drive member 19 to guide a helical relative movement of the piston rod 17 with respect to the drive member 19.

A generally cylindrical clutch 24 is disposed around the drive member 19, and the clutch 24 is at least partially surrounded by an end stop 28. The clutch 24 is located adjacent to the proximal end of the drive member 19. Saw teeth 29 are arranged in azimuthal sequence at the distal end of the clutch 24, and further saw teeth 31 are arranged in azimuthal sequence at the proximal end of the clutch 24. The clutch 24 is keyed to the drive member 19 by splines preventing a rotation of the clutch 24 relatively to the drive member 19. The clutch 24 is provided with a plurality of flexible arms that engage a plurality of splines on an interior surface of a dose dial sleeve 27.

A clutch plate 25 and a biasing means 26 are located between the distal end of the clutch 24 and a radially extending flange at the distal end of the drive member 19. The biasing means 26 may be a helical spring, for instance. The clutch plate 25 is rotationally locked to the housing 3. The proximal face of the clutch plate 25 is provided with saw teeth interacting with the saw teeth 29 at the distal end of the clutch 24 during the operation of dose setting.

An end stop 28 is disposed between the drive member 19 and the dose dial sleeve 27. The end stop 28 is rotationally locked to the housing 3 and is free to move axially with respect to the housing 3. In this embodiment, the external surface of the end stop 28 is provided with a helical groove or thread, which is engaged with a threaded insert 33 of the dose dial sleeve 27. The insert 33 is retained within the dose dial sleeve 27 by means of an end cap 34, which is locked both rotationally and axially with respect to the dose dial sleeve 27. Splines of the end stop 28 may be provided to engage with the clutch plate 25, thus locking the clutch plate 25 rotationally with respect to the housing 3.

The dose dial sleeve 27 is provided with an outer helical thread 41 guiding a helical movement of the dose dial sleeve 27 with respect to the housing 3. A dose dial grip 46 is disposed at the proximal end 30 of the dose dial sleeve 27 and is provided with a central opening. A button 49 is provided at the proximal end 30 of the drug delivery device 1. The button 49 extends through the central opening of the dose dial grip 46 and enters the bearing 22 of the drive member 19.

The first screw thread 15 of the piston rod 17 is guided by the screw thread 8 on the inner wall of the hole 5 of the guide nut 4. The guide nut 4 is prevented from axial movement with respect to the housing 3 by means of a web 32 and a part of the interaction member 14 (not shown in detail, see context of FIG. 6). This means, a part of the interaction member 14 prevents axial movement of the guide nut 4 in distal direction, whereby the web 32 prevents axial movement of the guide nut 4 in proximal direction. The web 32 can be provided by interfaces or protruding elements formed by integral parts of the housing 3 extending transversely to the axis of the piston rod 17 into the interior volume of the housing 3. The web 32 can instead be formed by separate components that are fastened to the housing 3, e.g. by parts of the carrier 11 of the resilient member 10 (see FIG. 5). The form of the web 32 is only restricted by its function to secure the guide nut 4 against an axial shift in proximal direction with respect to the housing 3. To this end, the web 32 comprises parts located on the proximal side of the guide nut 4, as can be seen from FIG. 8. The locking means 9 can be mounted on the inner wall of the housing 3 or to an insert that is stationary with respect to the housing 3, e.g. the carrier 11 of the resilient member The locking means 9 can be mounted on the inner wall of the housing 3 or to an insert that is stationary with respect to the housing 3, e.g. the carrier 11 of the resilient member 10. The interaction member 14 is arranged such that it can operate the locking means 9 according to the principle explained in the context of FIG. 6. In particular, the cartridge holder 2 may interact with the interaction member 14 such that the interaction member 14 may be rotated via a rotation of the cartridge holder 2, when the cartridge holder 2 is connected to the housing 3 as described in connection with FIGS. 8 to 11. When the cartridge holder 2 is firmly connected to the housing 3, the guide nut 4 is rotationally locked to the housing 3 by the engaged locking means 9. When the cartridge holder 2 is removed, the guide nut 4 is released and free to rotate relatively to the housing 3.

When the guide nut 4 is rotationally locked to the housing 3, the movement of the piston rod 17 is guided by the screw thread 8 of the guide nut 4 engaging the first screw thread 15 of the piston rod 17. The movement of the piston rod 17 is thus restricted to a helical movement relatively to the housing 3. When the guide nut 4 is not rotationally locked to the housing 3, the movement of the piston rod 17 is no longer restricted by the guide nut 4. As the guide nut 4 is still not able to move axially because of the interaction member 14 and the web 32, an axial shift of the piston rod 17 with respect to the housing 3 requires a corresponding helical movement with respect to the guide nut 4. This helical movement is easily generated, because the disengagement of the guide nut 4 from the locking means 9 enables the guide nut 4 to rotate freely and with low friction with respect to the housing 3 in a way to permit the movement of the piston rod 17.

The operation of the described embodiment of the drug delivery device will be described in the following.

To set a dose to be delivered, the user rotates the dose dial grip 46, thereby rotating the dose dial sleeve 27. The clutch 24 is engaged with the dose dial sleeve 27 by means of the saw teeth 31 at the proximal end of the clutch 24. This engagement and the splined engagement of the clutch 24 and the drive member 19 make the clutch 24 and the drive member 19 rotate with the dose dial sleeve 27. The clutch plate 25 is pushed towards the clutch 24 by the biasing means 26 in order to keep the saw teeth 29 of the clutch 24 and the saw teeth of the clutch plate 25 in contact. The profile of the saw teeth enables the relative movement of the clutch 24 and the clutch plate 25, which is rotationally locked to the housing 3, and this relative movement provides an audible and tactile feedback of the set operation. The setting of a unit or a specified subunit of a dose can thereby be indicated, if the saw teeth are dimensioned accordingly.

The larger the dose to be set, the farther the dose dial sleeve 27 is moved out of the housing 3. The relative movement of the dose dial sleeve 27 with respect to the housing 3 is helical, because the coupling is effected by means of a screw thread. The pitch of the outer helical thread 41 of the dose dial sleeve 27, the pitch of the second screw thread 16 of the piston rod 17, and the coupling between the dose dial sleeve 27 and the piston rod 17 are adapted to enable the helical movement of the dose dial sleeve 27 with respect to the housing 3 while leaving the piston rod 17 stationary with respect to the housing 3. The piston rod 17 is maintained at its position during the set operation, because the movement of the piston rod 17 is restricted by the engaged guide nut 4.

The end stop 28, which is coupled to the dose dial sleeve 27 but prevented from rotating with respect to the housing 3, moves in the proximal direction when the dose dial sleeve 27 is rotated out of the housing 3. When a dose is set equal to the remaining dispensable contents of the cartridge 6, the end stop 28 abuts a stop means 36 of the piston rod 17, which prevents the end stop 28 and simultaneously the dose dial sleeve 27 from moving further in the proximal direction, and the set operation is stopped.

If the set dose is too large, the set operation can be corrected by rotating the dose dial grip 46 in the opposite direction. The reverse rotation of the clutch 24 makes the saw teeth of the clutch 24 override the saw teeth of the clutch plate 25.

When the desired dose has been set, it can be dispensed by pressing the button 49 in the distal direction. This displaces the clutch 24 in the distal direction with respect to the dose dial sleeve 27, thereby decoupling the clutch 24 and simultaneously the drive member 19 from the dose dial sleeve 27. The clutch 24 remains rotationally locked to the drive member 19. The dose dial sleeve 27 is now free to move helically back in the distal direction without causing a rotational or helical movement of the drive member. The displacement of the clutch 24 also moves the clutch plate 25 in the distal direction against the biasing means 26, until the clutch plate 25 abuts a shoulder on the drive member 19. The clutch 24 and the clutch plate 25 are thereby engaged, so that a rotation of the clutch 24 relatively to the clutch plate 25 is prevented. A rotation of the clutch 24 and the drive member 19 with respect to the housing 3 is thus also inhibited, because the clutch plate 25 is rotationally locked to the housing 3 by means of the end stop 28. The clutch plate 25, the clutch 24 and the drive member 19 are moved together in the distal direction but do not rotate with respect to the housing 3.

The movement of the drive member 19 causes a helical movement of the piston rod 17 with respect to the housing 3 by means of the second screw thread 16 engaging the inner screw thread of the drive member 19. As the movement of the piston rod 17 is also guided by the first screw thread 15 engaging the inner screw thread 8 of the guide nut 4, and the guide nut 4 is presently engaged with the locking means 9 and thus rotationally locked to the housing 3, the helical movement of piston rod 17 advances the piston rod 17 in the distal direction. The ratio of the pitches of the first screw thread 15 and the second screw thread 16 can be selected according to a desired proportion between the distance by which the drive member 19 is shifted and the distance by which the piston rod 17 is shifted relatively to the housing 3 during the dispense operation. The movement of the dose dial sleeve 27 in the distal direction causes the end stop 28 to move back to its initial position within the housing 3.

When the cartridge 6 is empty, it may be substituted with a new one. To this purpose, the cartridge holder 2 is removed from the housing 3 as described above, the empty cartridge 6 is taken out of the cartridge holder 2, and a new cartridge is inserted. Before the cartridge holder 2 is attached to the housing 3, the piston rod 17 is reset to a start position, which is appropriate in view of the location that is occupied by the bung 7 when the cartridge holder 2 is attached.

The piston rod 17 is reset in the proximal direction. The movement of the piston rod 17 is restricted by the first screw thread 15 and the second screw thread 16 engaging the guide nut 4 and the drive member 19, respectively. When both the guide nut 4 and the drive member 19 are stationary with respect to the housing 3, a movement of the piston rod 17 relatively to the housing 3 is not possible because the first screw thread 15 and the second screw thread 16 do not have the same pitch and sense of rotation. The reset of the piston rod 17 by an axial movement in the proximal direction is possible when the guide nut 4 is free to rotate relatively to the housing 3, thus enabling a helical movement of the guide nut 4 with respect to the piston rod 17 irrespective of the position and movement of the piston rod 17 with respect to the housing 3.

The reset operation is therefore made possible by a release of the guide nut 4. As the interaction member 14 is operated by the cartridge holder 2, the locking means 9 is disengaged from the guide nut 4 due to interaction with the interaction member 14, as long as the cartridge holder 2 is not attached to the housing 3. When the piston rod 17 is shifted in the proximal direction, the guide nut 4 rotates according to the required helical movement of the guide nut 4 with respect to the piston rod 17. When the piston rod 17 is reset, the cartridge holder 2 is attached to the housing 3. The interaction member 14 is rotated by means of mechanical cooperation with the cartridge holder 2 as described above, and enables the locking means 9 to engage with the guide nut 4, so that the guide nut 4 is rotationally locked to the housing 3. The drug delivery device is then ready for further operation as described above.

The reset of the piston rod 17 can be performed manually, while the cartridge holder 2 stays completely removed. The reset can be achieved by pushing the piston rod 17 towards the proximal end 30 or by holding the device 1 with the proximal end 30 pointing down to have the gravitational force move the piston rod 17 to the reset position. Instead, the piston rod 17 can be pushed by the bung 7 to the reset position, when the cartridge holder 2 is being attached and approaches the proximal end 30.

The details of this embodiment in their entirety do not represent the essential features of the disclosure and do not restrict the scope of the disclosure as claimed. Various modifications, alterations and substitutions of the drive assembly and the drug delivery device are within the scope of the disclosure.

The invention claimed is:

1. An assembly for a drug delivery device comprising
a housing,
a cartridge holder releasably connectable to the housing,
a resilient member having a ring-shaped carrier having a center portion and a locking means comprising at least one spring arm having a fixed end and free end, where the free end can pivot about the fixed end to flex radially inward towards the center portion,
an interaction member which is configured to mechanically cooperate with the resilient member and with the cartridge holder,
a guide nut encompassed by the resilient member and the interaction member to prevent axial movement of the guide nut relative to the housing, wherein an exterior of the guide nut comprises a plurality of teeth and notches and a center hole coupled with a piston rod to cause a predetermined axial movement of the piston rod relative to the housing during drug delivery,
wherein the resilient member or an additional resilient member is configured to rotationally bias the interaction member, wherein the assembly has a locked state where the cartridge holder is connected to the housing, the cartridge holder being obstructed from movement with respect to the housing with the locking means flexing radially inward to engage with one of the plurality of notches of the guide nut, and an unlocked state where the connection between the cartridge holder and the housing is released, the cartridge holder being freely moveable with respect to the housing,
and wherein, for switching from the unlocked state into the locked state, the cartridge holder is brought into mechanical cooperation with the interaction member, the cartridge holder is rotated in a first direction with respect to the housing, the interaction member thereby being rotated in the first direction such that the interaction member mechanically cooperates with the resilient member and such that a rotational force exerted on the interaction member by means of the resilient member is overcome for switching the assembly from the unlocked state into the locked state.

2. The assembly according to claim 1, wherein in the locked state, the interaction member is rotationally locked with respect to the housing by mechanical cooperation with the resilient member, and wherein in the unlocked state, the interaction member is rotatable with respect to the housing.

3. The assembly according to claim 2, wherein the resilient member is configured to provide a radially inwards directed force onto the interaction member which is great enough to rotationally lock the interaction member and the resilient member such that rotation of the interaction member in a second direction is prevented when the assembly is in the locked state.

4. The assembly according to claim 3, wherein, for switching from the locked state into the unlocked state, the cartridge holder is rotated in the second direction, the rotational force provided on the cartridge holder thereby being greater than a rotational counter force provided onto the interaction member by means of the resilient member such that said counterforce is overcome and such that the rotational lock between the interaction member and the resilient member is released.

5. The assembly according to claim 1, providing an axially directed force onto the cartridge holder such that, in the unlocked state, the cartridge holder is set apart from the housing.

6. The assembly according to claim 5, wherein the axially directed force is provided by the resilient member or by at least one additional spring member.

7. The assembly according to claim 1, wherein the resilient member is secured against rotation with respect to the housing.

8. The assembly according to claim 1, wherein the resilient member comprises at least one snap feature and, the interaction member comprises at least one corresponding interaction snap feature, and wherein, in the locked state, the snap feature and the interaction snap feature are configured to abut.

9. The assembly according to claim 8, wherein the snap feature is part of or is integrally formed with a radially resilient spring arm of the resilient member.

10. The assembly according to claim 8, wherein the interaction snap feature comprises a bump, and wherein the interaction snap feature is arranged on an outer surface of the interaction member, and wherein the snap feature comprises a bump.

11. The assembly according to claim 1, wherein, in the locked state of the assembly, axial movement of the cartridge holder with respect to the housing is prevented by mechanical cooperation of a first fastening means of the cartridge holder and a second fastening means of the housing.

12. The assembly according to claim 11, wherein mechanical cooperation of the first fastening means and the second fastening means is configured to limit the rotation of the cartridge holder in the first direction and in a second direction with respect to the housing.

13. The assembly according to claim 11, wherein the first and the second fastening means are configured such that axial movement of the cartridge holder with respect to the housing is allowed when the assembly is switched from the locked state into the unlocked state.

14. The assembly according to claim 1, wherein the interaction member comprises at least one first coupling member adapted and arranged for engagement with at least one corresponding second coupling member of the cartridge holder for rotationally locking the interaction member and the cartridge holder.

15. The assembly according to claim 1, wherein the interaction member is secured against axial movement with respect to the housing.

16. The assembly according to claim 1, wherein the interaction member comprises a ring-like shape.

17. The assembly according to claim 1, wherein the resilient member is at least in parts circumferentially arranged on at least a part of an exterior of the interaction member.

18. The assembly according to claim 1, wherein the interaction member is rotationally locked with respect to the housing by mechanical cooperation with the resilient member and wherein when the assembly is switched from the locked state to the unlocked state the resilient member or a further resilient member rotationally biases the interaction member into a second direction opposite to the first direction.

19. The assembly according to claim 1, wherein the at least one spring arm has a hook on a free end, the interaction member has a main body having at least one radial recess, and the cartridge holder is obstructed from movement with respect to the housing with the hook extending through the at least one radial recess and engaged with one of the plurality of notches of the guide nut.

20. A drug delivery device comprising the assembly according to claim 1 and a cartridge, wherein the cartridge is retained in the cartridge holder, and wherein the cartridge comprises a plurality of doses of a drug.

* * * * *